United States Patent [19]

Nedelec et al.

[11] 4,213,989

[45] Jul. 22, 1980

[54] ANOREXIGENIC 3-PHENYL-TETRAHYDROPYRIDINES

[75] Inventors: Lucien Nedelec, Le Raincy; Jacques Guillaume, Sevran; Claude Dumont, Nogent-sur-Marne, all of France

[73] Assignee: Roussel Uclaf, Paris, France

[21] Appl. No.: 9,234

[22] Filed: Feb. 2, 1979

[30] Foreign Application Priority Data

Feb. 8, 1978 [FR] France .................. 78 03526

[51] Int. Cl.² .................. A61K 31/44; C07D 211/70
[52] U.S. Cl. .................. 424/263; 546/216; 546/326; 546/346
[58] Field of Search .................. 546/346; 424/263

[56] References Cited

U.S. PATENT DOCUMENTS

| | | | |
|---|---|---|---|
| 3,125,488 | 3/1964 | Biel | 546/346 X |
| 3,221,017 | 11/1965 | Biel | 546/346 X |
| 3,284,457 | 11/1966 | Beschke et al. | 546/346 |

FOREIGN PATENT DOCUMENTS 1530061  10/1978  United Kingdom .

*Primary Examiner*—Henry R. Jiles

*Assistant Examiner*—Richard A. Schwartz
*Attorney, Agent, or Firm*—Hammond & Littell, Weissenberger and Muserlian

[57] ABSTRACT

Novel 3-phenyl-tetrahydropyridines of the formula

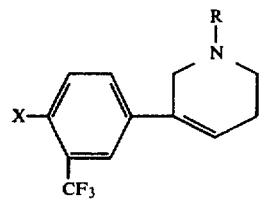

wherein X is selected from the group consisting of hydrogen and chlorine and R is selected from the group consisting of hydrogen, alkyl of 1 to 5 carbon atoms, alkenyl and alkynyl of 3 to 5 carbon atoms and phenyl alkyl of 1 to 3 alkyl carbon atoms with the proviso that X is not hydrogen when R is benzyl and their non-toxic, pharmaceutically acceptable acid addition salts having remarkable anorexigenic properties and inhibition of serontine collection both in vivo and in vitro and their preparation and novel intermediates.

6 Claims, No Drawings

ANOREXIGENIC 3-PHENYL-TETRAHYDROPYRIDINES

STATE OF THE ART

U.S. Pat. No. 4,046,901 and No. 4,072,685 of the assignee of the present application and Belgium Pat. No. 851,350 disclose related pyridine compounds.

OBJECTS OF THE INVENTION

It is an object of the invention to provide the novel compounds of formula I and their non-toxic, pharmaceutically acceptable acid addition salts.

It is another object of the invention to provide a novel process for the preparation of the compounds of formula I and to novel intermediates produced thereby.

It is an additional object of the invention to provide novel anorexigenic compositions and to a novel method of curbing the appetite of warm-blooded animals.

These and other objects and advantages of the invention will become obvious from the following detailed description.

THE INVENTION

The novel compounds of the invention are selected from the group consisting of 3-phenyl-tetrahydropyridines of the formula

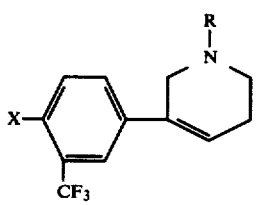

wherein X is selected from the group consisting of hydrogen and chlorine and R is selected from the group consisting of hydrogen, alkyl of 1 to 5 carbon atoms, alkenyl and alkynyl of 3 to 5 carbon atoms and phenyl alkyl of 1 to 3 alkyl carbon atoms with the proviso that X is not hydrogen when R is benzyl and their non-toxic, pharmaceutically acceptable acid addition salts.

Examples of R in formula I are alkyl of 1 to 5 carbon atoms such as methyl, ethyl, propyl, isopropyl, butyl, isobutyl and pentyl; alkenyl and alkynyl of 3 to 5 carbon atoms such as allyl and propargyl; phenyl alkyl such as benzyl, phenethyl and 2-phenyl-propyl.

Examples of acids suitable for the formation of non-toxic, pharmaceutically acceptable acid addition salts are inorganic acids such as hydrochloric acid, hydrobromic acid, hydroiodic acid, nitric acid, sulfuric acid or phosphoric acid and inorganic acids such as acetic acid, formic acid, benzoic acid, maleic acid, fumaric acid, succinic acid, tartaric acid, citric acid, oxalic acid, glyoxylic acid and aspartic acid; alkane sulfonic acids such as methane sulfonic acid and arylsulfonic acid such as benzene sulfonic acid.

Among the preferred compounds of formula I are those wherein X is hydrogen and those wherein X is hydrogen and R is hydrogen or alkyl of 1 to 5 carbon atoms and their non-toxic, pharmaceutically acceptable acid addition salts. Specific preferred compounds are 3-(3-trifluoromethyl-phenyl)-1,2,5,6-tetrahydropyridine hydrochloride, 1-propyl-3-(3-trifluoromethyl-phenyl)-1,2,5,6-tetrahydropyridine hydrochloride and 1-isopropyl-3-(3-trifluoromethyl-phenyl)-1,2,5,6-tetrahydropyridine hydrochloride.

The novel process of the invention for the preparation of the compounds of formula I comprises subjecting a compound of the formula

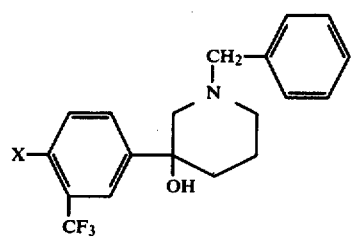

to deshydration to obtain a compound of the formula

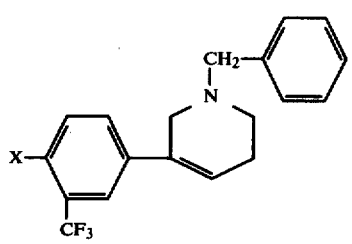

which may be recovered and, if desired, salified with an acid or reacted with an alkyl chloroformate of the formula

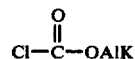

wherein AlK is alkyl of 1 to 3 carbon atoms to obtain a compound of the formula

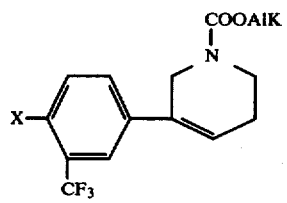

and saponifying the latter to obtain a compound of the formula

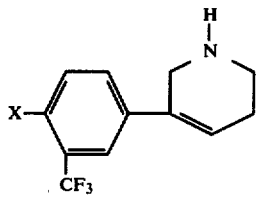

which may be isolated and, if desired, salified with an acid or reacted with a halide of the formula R'—Hal     V wherein R' is R other than hydrogen to obtain a compound of the formula

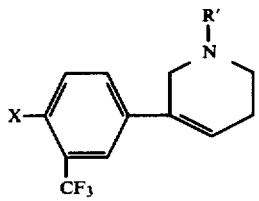

which, if desired, may be salified with an acid.

In a preferred embodiment of the process of the invention, the deshydration is effected with an energetic deshydration agent such as polyphosphoric acid, anhydrous phosphoric acid or p-toluene sulfonic acid in a refluxing organic solvent such as xylene. The reaction with the alkyl chloroformate is preferably effected at reflux in an organic solvent such as benzene and the saponification may be effected at reflux with an alkali metal hydroxide such as sodium hydroxide or potassium hydroxide in an organic solvent such as butanol. The reaction with the halide of formula V is preferably effected in an organic solvent such as acetone in the presence of silver oxide or sodium carbonate.

In a variation of the process of the invention for the preparation of a compound of formula I wherein X and R are hydrogen, a hydrochloride of a compound of the formula

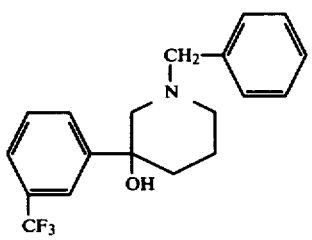

is subjected to hydrogenolysis to obtain the hydrochloride of a compound of the formula

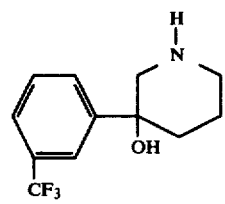

and subjecting the latter to deshydration to form a compound of the formula

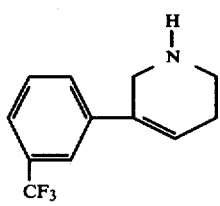

which may be salified, if desired.

In a preferred mode of the process, the hydrogenolysis is effected with hydrogen in the presence of a catalyst such as palladium hydroxide in a low molecular weight alkanol such as methanol or ethanol. The deshydration is effected with an energetic deshydration agent such as polyphosphoric acid, phosphoric acid anhydride or p-toluene sulfonic acid in a refluxing organic solvent such as xylene.

The compounds of formula I have a basic character and may be salified by reacting substantially stoichiometric proportions of the base and the desired acid.

The novel anorexigenic compositions of the invention are comprised of an anorexigenically effective amount of at least one compound of formula I and its non-toxic, pharmaceutically acceptable acid addition salts and an inert pharmaceutical carrier or excipient. The compositions may be in the form of tablets, dragees, gelules, granules, suppositories and injectable solutions or suspensions. Examples of suitable excipients are talc, gum arabic, lactose starch, magnesium stearate, cocao butter, aqueous and non-aqueous vehicles, fatty bodies of animal or vegetable origin, paraffinic derivatives, glycols, diverse wetting agents, dispersants or emulsifiers and preservatives.

The compositions are useful for the treatment of simple or complicated obesity in adults or adolescents as well as in the treatment of depression, melancholy, manic-depressive psychoses, reactionary depression, exhaustion and neurotic depression since they also inhibit serotonine up take.

Among the preferred compositions are those wherein X is hydrogen and those wherein X is hydrogen and R is hydrogen or alkyl of 1 to 5 carbon atoms and their non-toxic, pharmaceutically acceptable acid addition salts. Specific preferred compounds are 3-(3-trifluoromethyl-phenyl)-1,2,5,6-tetrahydropyridine hydrochloride, 1-propyl-3-(3-trifluoromethyl-phenyl)-1,2,5,6-tetrahydropyridine hydrochloride and 1-isopropyl-3-(3-trifluoromethyl-phenyl)-1,2,5,6-tetrahydropyridine hydrochloride.

The novel method of curbing the appetite of warm-blooded animals, including humans, comprises administering to warm-blooded animals an anorexigenically effective amount of at least one compound of formula I and its non-toxic, pharmaceutically acceptable acid addition salts. The compounds may be administered orally, rectally or parenterally and the usual daily dose is 0.2 to 10 mg/kg depending upon the compound and method of administration.

The novel intermediates of the invention have a formula selected from the group consisting of

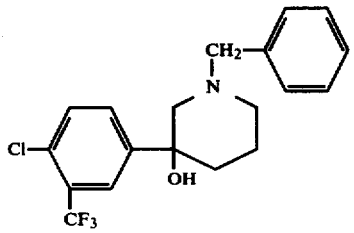

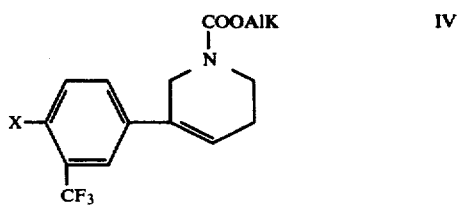

wherein X and AlK have the above definitions and

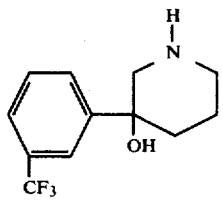

VI

The compound of formula II wherein X is hydrogen may be prepared by the process described in published French patent application Ser. No. 2,340,734. The product of formula IIb may be prepared by condensing the magnesium derivative of 2-chloro-5-bromo-trifluoromethyl benzene and N-benzyl-3-piperidone.

In the following examples there are described several preferred embodiments to illustrate the invention. However, it should be understood that the invention is not intended to be limited to the specific embodiments.

EXAMPLE 1

3-(4-chloro-3-trifluoromethyl-phenyl)-1-benzyl-1,2,5,6-tetrahydropyridine hydrochloride

STEP A:

3-(4-chloro-3-trifluoromethyl-phenyl)-1-benzyl-piperidine-3-ol hydrochloride 15 ml of anhydrous, distilled tetrahydrofuran were added to 3 g of magnesium turnings activated by iodine sublimation and a few drops of a solution of 30 g of 2-chloro-5-bromo-trifluoromethyl-benzene in 60 ml of tetrahydrofuran were added thereto. The rest of the solution was then added over one hour in a manner to maintain reflux of the mixture and then the mixture was refluxed for 30 more minutes and was allowed to stand for one hour. The magnesium mixture was placed in an ice bath and a solution of 12 g of N-benzyl-3-piperidone (obtained from its hydrochloride) in 35 ml of anhydrous tetrahydrofuran was added dropwise thereto over 15 minutes under an inert atmosphere at a temperature less than 10° C. The mixture was stirred at room temperature for 16 hours and was cooled on an ice bath while adding thereto dropwise 15 ml of an aqueous ammonium chloride solution. The mixture was filtered and was extracted with ethyl acetate. The decanted aqueous phase was extracted again with ethyl acetate and the combined organic phases were washed with water, dried over magnesium sulfate and evaporated to dryness under reduced pressure. The raw residue was dissolved in 50 ml of ethyl acetate and a solution of gaseous hydrogen chloride in ethyl acetate was added thereto until the pH was acidic. The mixture was iced for 2 hours and was vacuum filtered. The recovered product was washed with ethyl acetate and dried under reduced pressure to obtain 25 g of 3-(4-chloro-3-trifluoromethyl-phenyl)-1-benzyl-piperidine-3-ol melting at ≈230° C.

STEP B:

3-(4-chloro-3-trifluoromethyl-phenyl)-1-benzyl-1,2,5,6-tetrahydropyridine hydrochloride A suspension of 25 g of the product of Step A in about 10 volumes of water cooled in an ice bath was made basic by addition of ammonium hydroxide and the mixture was extracted with ethyl acetate. The organic extract was washed with water, dried over magnesium sulfate and evaporated to dryness under reduced pressure to obtain 22 g of 3-(4-chloro-3-trifluoromethyl-phenyl)-1-benzyl-1,2,5,6-tetrahydropyridine which were dissolved in 250 ml of anhydrous xylene. The solution was refluxed for 5 hours with vigorous stirring while adding 10 g of phosphoric acid anhydride each hour for a total of 50 g and the mixture was allowed to stand overnight at room temperature. Then, ice was continuously added to the reaction mixture and the mass formed was dissolved in a mixture of water, ethyl acetate and triethylamine. After total dissolution, it was ascertained that the mixture was basic and the organic phase was washed with aqueous sodium chloride solution. The wash water was extracted with ethyl acetate and the combined organic phases were dried over magnesium sulfate and evaporated to dryness under reduced pressure. The residue was chromatographed over silica gel and was eluted with a 9-1 cyclohexane-ethyl acetate mixture. The fractions corresponding to the desired product were distilled to dryness and the residue was taken up in methylene chloride. The solution was filtered and the filtrate was evaporated to dryness under reduced pressure to obtain 17 g of the said base. 7 g of the base were dissolved in 50 ml of ethyl acetate and a solution of gaseous hydrogen chloride in ethyl acetate was added thereto dropwise until the pH was acidic. The mixture was iced for 2 hours and was vacuum filtered and the recovered product was washed with ethyl acetate and was dried under reduced pressure to obtain 6.37 g of the desired hydrochloride which was crystallized from isopropanol to obtain 5.25 g of the product melting at 200° C.

Analysis: $C_{19}H_{18}Cl_2F_3N$; molecular weight = 382.276; Calculated: %C 58.78, %H 4.67, %N 3.61, %F 14.68, %Cl 18.26; Found: 58.9, 4.6, 3.6, 14.6, 18.0.

EXAMPLE 2

3-(3-trifluoromethyl-phenyl)-1,2,5,6-tetrahydro-pyridine hydrochloride

STEP A: 3-(3-trifluoromethyl-phenyl)-piperidine-3-ol hydrochloride

A solution of gaseous hydrogen chloride in ethyl acetate was added dropwise to a solution of 64 g of 1-benzyl-3-(3-trifluoromethyl-phenyl)-piperidine-3-ol in 100 ml of ethyl acetate until the pH was acidic and the mixture was vacuum filtered. The recovered product was washed with ethyl acetate and was dried under reduced pressure to obtain 62.5 g of 1-benzyl-3-(3-trifluoromethyl-phenyl)-piperidine-3-ol hydrochloride which sublimed towards 240° C. A suspension of 60 g of the said hydrochloride in 2.4 liters of ethanol was admixed with 12 g of activated carbon containing 10% by weight of palladium hydroxide and 4.2 liters of hydrogen was bubbled therethrough at 20° C. in 2 hours. The mixture was filtered and the filtrate was evaporated to dryness under reduced pressure. The residue was crystallized from 100 ml of methanol and the mixture was vacuum filtered at 5° C. The recovered product was washed with iced methanol and dried at 35° C. to obtain 43.6 g of 3-(3-trifluoromethyl-phenyl)-piperidine-3-ol hydrochloride melting at 210° C.

Analysis: $C_{12}H_{15}ClF_3NO$; molecular weight = 281.715; Calculated: %C 51.16, %H 5.37, %Cl 12.59, %F 20.23, %N 4.97; Found: 51.2, 5.3, 12.7, 19.9, 4.9.

STEP B:
3-(3-trifluoromethyl-phenyl)-1,2,5,6-tetrahydropyridine

A suspension of 39 g of the product of Step A in 400 ml of xylene was heated under an inert atmosphere with stirring to 100° C. and 28.7 g of phosphoric acid anhydride were added thereto over 2 minutes. The temperature was raised to 110° C. and was heated there for 15 minutes and was allowed to cool to room temperature overnight. Several times the resulting resin was taken up in a mixture of water, ethyl acetate and trimethylamine. The mixture was stirred and the decanted organic phase was washed with aqueous sodium chloride solution, was dried, filtered and evaporated to dryness under reduced pressure. The residue was dissolved in 50 ml of ethyl acetate and 70 ml of an ethyl acetate solution saturated with gaseous hydrogen chloride was added thereto at 15°–20° C. The mixture was concentrated under reduced pressure and was vacuum filtered. The recovered product was washed with ether, with a 50–50 ether-ethyl acetate mixture and with ethyl acetate and was dried at 35° C. to obtain 23.7 g of product which was crystallized from ethanol to obtain 18.3 g of 3-(3-trifluoromethyl-phenyl)-1,2,5,6-tetrahydropyridine hydrochloride melting at 230° C. (decomposition). Evaporation of the mother liquors yielded another 2.4 g of the said product melting at 230° C. (decomposition).

Analysis: $C_{12}H_{13}ClF_3N$; molecular weight=263.699; Calculated: %C 54.66, %H 4.97, %Cl 13.45, %F 21.62, %N 5.31; Found: 54.5, 5.2, 13.5, 21.5, 5.4.

EXAMPLE 3
1-propyl-3-(3-trifluoromethyl-phenyl)-1,2,5,6-tetrahydropyridine hydrochloride A solution of 10 g of the product of Example 2 in 200 ml of water was made alkaline by addition of sodium carbonate and the mixture was extracted with ethyl acetate. The organic phase was washed with aqueous sodium chloride solution, was dried and evaporated to dryness to obtain 9 g of free base. A mixture of 4.44 g of the said product in 22 ml of acetone was stirred under an inert atmosphere while adding 2 g of silver oxide and 2 ml of propyl iodide and the mixture was stirred for 3 more hours after which 500 mg of silver oxide were added thereto. The mixture was stirred for 2 hours and was filtered. The recovered product was rinsed with ethyl acetate and dried under reduced pressure to obtain 4.9 g of raw 1-propyl-3-(3-trifluoromethyl-phenyl)-1,2,5,6-tetrahydropyridine. The said product was chromatographed over silica gel and was eluted with an 85–10–5 cyclohexane-chloroform-triethylamine mixture to obtain 4.35 g of the said product.

IR Spectrum (chloroform): 1324 cm$^{-1}$ (CF$_3$); 1653, 1632, 1612, 1591 and 1490 cm$^{-1}$ (C=C and aromatics).

The said product was dissolved in 30 ml of ether and 10 ml of ethyl acetate saturated with gaseous hydrogen chloride were added thereto. The mixture was stirred at room temperature for 15 minutes and was filtered. The recovered product was washed with ether and the resulting 4.1 g were crystallized from ethyl acetate to obtain 3.5 g of the desired hydrochloride melting at 168°–170° C.

Analysis: $C_{15}H_{19}ClF_3N$; molecular weight=305.787; Calculated: %C 58.92, %H 6.26, %Cl 11.60, %F 18.64; %N 4.58; Found: 58.9, 6.2, 11.6, 18.3, 4.6.

EXAMPLE 4
1-isopropyl-3-(3-trifluoromethyl-phenyl)-1,2,5,6-tetrahydropyridine hydrochloride A mixture of 2.2 g of 3-(3-trifluoromethyl-phenyl)-1,2,5,6-tetrahydropyridine, 18 ml of acetone, 1.18 g of silver oxide and 1.4 ml of isopropyl iodide was stirred for 12 hours at room temperature and after the addition of 0.7 ml of isopropyl iodide and 0.5 g of silver oxide, the mixture was stirred another 3 hours at room temperature and was filtered. The filtrate was evaporated to dryness to obtain 2.9 g of raw product which was chromatographed over silica gel. Elution with an 85–10–5 cyclohexane-chloroform-triethylamine mixture yielded 2.21 g of 1-isopropyl-3-(3-trifluoromethyl-phenyl)-1,2,5,6-tetrahydropyridine in the form of a yellow oil.

A solution of the said 2.1 g in 20 ml of ethyl acetate was mixed with 10 ml of ethyl acetate saturated with gaseous hydrogen chloride and followed by the addition of 50 ml of ether. The mixture was stirred at room temperature for 30 minutes and was filtered. The recovered product was rinsed with ether to obtain 1.88 g of the desired hydrochloride which was crystallized from acetone to obtain 1.18 g of the hydrochloride melting at 190° C.

Analysis: $C_{15}H_{18}F_3ClN$; molecular weight=269.322; Calculated: %C 58.92, %H 6.26, %F 18.64, %Cl 11.6, %N 4.58; Found: 58.8, 6.5, 18.3, 11.6, 4.5

EXAMPLE 5
3-(4-chloro-3-trifluoromethyl-phenyl)-1,2,5,6-tetrahydropyridine hydrochloride

STEP A: ethyl 3-(4-chloro-3-trifluoromethyl-phenyl)-1,2,5,6-tetrahydropyridine-1-carboxylate 2.5 ml of distilled ethyl chloroformate were added to a mixture of 5 g of 3-(4-chloro-3-trifluoromethyl-phenyl)-1-benzyl-1,2,5,6-tetrahydropyridine and 55 ml of anhydrous, distilled benzene and the mixture was refluxed with stirring under an inert atmosphere for 5 hours. The mixture was evaporated to dryness to obtain 5 g of ethyl 3-(4-chloro-3-trifluoromethyl-phenyl)-1,2,5,6-tetrahydropyridine-1-carboxylate.

IR Spectrum (chloroform): 1690 cm$^{-1}$ (C=0); 1650, 1637 (shoulder), 1606 and 1570 cm$^{-1}$ (C=C and aromatic).

STEP B: 3-(4-chloro-3-trifluoromethyl-phenyl)-1,2,5,6-tetrahydropyridine hydrochloride A mixture of 5 g of the product of Step A, 5 g of potassium hydroxide pastilles and 50 ml of n-butanol was heated in a bath at 120° C. for 2 hours and was then allowed to cool to room temperature. The mixture was diluted with water and was extracted with ethyl acetate. The organic extract was washed with aqueous sodium chloride solution, dried and evaporated to dryness under reduced pressure to obtain 5.2 g of raw product. The latter was chromatographed over silica gel and was eluted with a 6–3–1 chloroform-acetone-triethylamine mixture. The fractions containing desired product were evaporated to dryness and the residue was dissolved in methylene chloride. The solution was filtered and the filtrate was evaporated to dryness under reduced pressure to obtain 3.5 g of product. The latter was dissolved in 10 volumes of ethyl acetate and an ethyl acetate solution saturated with gaseous hydrogen chloride was added thereto dropwise until the pH was acidic. The mixture was iced for 2 hours and was vacuum filtered. The product was washed with ethyl acetate and was dried under reduced pressure to obtain 3.68 g of 3-(4-chloro-3-trifluoromethyl-phenyl)-1,2,5,6-tetrahydropyridine hydrochloride melting at 258° C. The latter was crystallized from ethanol to obtain 2.94 g of the hydrochloride melting at 258° C.

Analysis: $C_{12}H_{12}Cl_2F_3N$; molecular weight=298.148; Calculated: %C 48.34, %H 4.06, %Cl 23.78, %F 19.12, %N 4.70; Found: 48.5, 4.1, 23.5, 19.1, 4.6.

EXAMPLE 6

Tablets were prepared containing either 25 mg of 3-(3-trifluoromethyl-phenyl)-1,2,5,6-tetrahydropyridine hydrochloride or 25 mg of 1-propyl-3-(3-trifluoromethylphenyl)-1,2,5,6-tetrahydropyridine hydrochloride and sufficient excipient of lactose, starch, talc and magnesium stearate for a final weight of 150 mg.

PHARMACOLOGICAL STUDY

Anorexigenic Activity in Dogs

The anorexigenic activity was studied in dogs using the method of Adams et al [J. Pharm. Sci., Vol. 53, (1964), p. 1405]. On the day of the test with the compound presumed to be anorexigenic, the individual daily ration of the animal was divided into about equal balls (10 to 20 g) which were offered to the dog every 10 minutes for 7 hours. Normally, the animal will regularly accept the successive balls when they are presented. Refusal shows anorexiant activity of the test compound which was administered in lieu of the first ball. In this test, the compounds of Examples 2 and 3 showed anorexigenic activity at a dose of 5 mg/kg.

Acute toxicity:

The $DL_{50}$ or lethal dose at which 50% of the animals died after intraperitoneal administration of the test compound to mice was determined 48 hours after the administration. The $DL_{50}$ for the compounds of Examples 1 and 2 was about 400 mg/kg and 150 mg/kg, respectively and for the compounds of Examples 3, 4 and was about 170, 65 and 100 mg/kg, respectively.

Various modifications of the products and processes of the invention may be made without departing from the spirit or scope thereof and it is to be understood that the invention is intended to be limited only as defined in the appended claims.

We claim:

1. A method of curbing the appetite of warm-blooded animals comprising administering to warm-blooded animals an anorexigenically effective amount of at least one compound selected from the group consisting of 3-phenyl-tetrahydro-pyridines of the formula

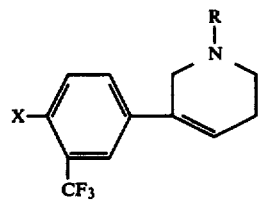

wherein X is selected from the group consisting of hydrogen and chlorine and R is selected from the group consisting of hydrogen, alkyl of 1 to 5 carbon atoms, alkenyl and alkynyl of 3 to 5 carbon atoms and phenyl alkyl of 1 to 3 alkyl carbon atoms with the proviso that X is not hydrogen when R is benzyl and their non-toxic, pharmaceutically acceptable acid addition salts.

2. The method of claim 1 wherein X is hydrogen.

3. The method of claim 2 wherein R is hydrogen or alkyl of 1 to 5 carbon atoms.

4. A method of claim 1 which is the hydrochloride of 3-(3-trifluoromethyl-phenyl)-1,2,5,6-tetrahydropyridine.

5. A method of claim 1 which is the hydrochloride of 1-propyl-3-(3-trifluoromethyl-phenyl)-1,2,5,6-tetrahydropyridine.

6. A method of claim 1 which is the hydrochloride of 1-isopropyl-3-(3-trifluoromethyl-phenyl)-1,2,5,6-tetrahydropyridine.

* * * * *